United States Patent
Kelly et al.

(10) Patent No.: US 7,096,062 B2
(45) Date of Patent: *Aug. 22, 2006

(54) METHOD FOR SELF-TEST OF DEFIBRILLATION AND PACING CIRCUITS INCLUDING A PATIENT ISOLATION SWITCH

(75) Inventors: Patrick F. Kelly, Edmonds, WA (US);
Paul S. Tamura, Seattle, WA (US);
Patricia Ewen, Seattle, WA (US);
Michelle C. Beyersdorf, Sammamish, WA (US)

(73) Assignee: Medtronic Physio-Control Manufacturing Corp., Redmond, WA (US)

( * ) Notice: Subject to any disclaimer, the term of this patent is extended or adjusted under 35 U.S.C. 154(b) by 750 days.

This patent is subject to a terminal disclaimer.

(21) Appl. No.: 10/141,687

(22) Filed: May 7, 2002

(65) Prior Publication Data

US 2003/0171779 A1 Sep. 11, 2003

Related U.S. Application Data

(63) Continuation-in-part of application No. 10/096,408, filed on Mar. 11, 2002, now Pat. No. 6,965,796.

(51) Int. Cl.
*A61N 1/08* (2006.01)

(52) U.S. Cl. .............. 607/4; 607/27; 607/63; 607/6

(58) Field of Classification Search ........... 507/4, 507/5, 6, 8, 62, 28, 63, 27; 600/547

See application file for complete search history.

(56) References Cited

U.S. PATENT DOCUMENTS

| 1,662,771 A | 3/1928 | Whittingham |
| 1,840,168 A | 1/1932 | Mucher |
| 1,841,332 A | 1/1932 | Kranz |
| 2,298,315 A | 10/1942 | Siegel et al. |
| 2,464,820 A | 3/1949 | Livera |
| 4,038,628 A | 7/1977 | Salemi |
| 4,274,136 A | 6/1981 | Onodera et al. |

(Continued)

FOREIGN PATENT DOCUMENTS

EP 0 315 768 A2 5/1989

(Continued)

OTHER PUBLICATIONS

G.H. Bardy et al., "Multicenter Comparison of Truncated Biphasic Shocks and Standard Damped Sine Wave Monophasic Shocks for Transthoracic Ventricular Defibrillation," *Circulation* 94(10):2507-2514, Nov. 15, 1996.

(Continued)

*Primary Examiner*—Kennedy Schaetzle

(57) ABSTRACT

A method and apparatus for performing self-tests on defibrillation and pacing circuits including a patient isolation switch is disclosed. Tests are provided for the defibrillation and pacing circuitry as well as the isolation switch. For testing the defibrillation circuitry, the impedance drive circuits and preamplifier may be utilized such that the energy storage capacitor is not required to be charged and discharged during the test, thus conserving energy. For testing the pacing circuitry and the isolation switch, the defibrillation circuitry is utilized. For certain of the tests, the test stimulus is the output voltage on the energy storage capacitor, while for other tests the test stimulus may be the pace current as indicated by the voltage across the input to the preamplifier. Alternative tests may be performed depending on whether the impedance at the output of the defibrillator is determined to be an open circuit or a short circuit.

16 Claims, 14 Drawing Sheets

U.S. PATENT DOCUMENTS

| | | |
|---|---|---|
| 4,402,322 A | 9/1983 | Duggan |
| 4,693,253 A | 9/1987 | Adams |
| 4,800,883 A | 1/1989 | Winstrom |
| 4,821,723 A | 4/1989 | Baker, Jr. et al. |
| 4,850,357 A | 7/1989 | Bach, Jr. |
| 5,048,521 A | 9/1991 | Pless et al. |
| 5,083,562 A | 1/1992 | de Coriolis et al. |
| 5,099,844 A | 3/1992 | Faupel |
| 5,225,769 A | 7/1993 | Fincke et al. |
| 5,233,986 A | 8/1993 | Robson |
| 5,249,573 A | 10/1993 | Fincke et al. |
| 5,275,158 A | 1/1994 | Lopin |
| 5,358,512 A | 10/1994 | Hoegnelid et al. |
| 5,376,103 A | 12/1994 | Anderson et al. |
| 5,431,682 A | 7/1995 | Hedberg |
| 5,431,684 A | 7/1995 | Archer et al. |
| 5,431,686 A | 7/1995 | Kroll et al. |
| 5,441,518 A | 8/1995 | Adams et al. |
| 5,468,254 A | 11/1995 | Hahn et al. |
| 5,470,341 A | 11/1995 | Kuehn et al. |
| 5,489,293 A | 2/1996 | Pless et al. |
| 5,507,781 A | 4/1996 | Kroll et al. |
| 5,514,160 A | 5/1996 | Kroll et al. |
| 5,522,853 A | 6/1996 | Kroll |
| 5,531,765 A | 7/1996 | Pless |
| 5,534,015 A | 7/1996 | Kroll et al. |
| 5,561,213 A | 10/1996 | Poessnecker |
| 5,591,209 A | 1/1997 | Kroll |
| 5,591,210 A | 1/1997 | Kroll et al. |
| 5,591,211 A | 1/1997 | Meltzer |
| 5,591,213 A | 1/1997 | Morgan |
| 5,593,427 A | 1/1997 | Gliner et al. |
| 5,601,608 A | 2/1997 | Mouchawar |
| 5,601,612 A | 2/1997 | Gliner et al. |
| 5,607,454 A | 3/1997 | Cameron et al. |
| 5,620,465 A | 4/1997 | Olson et al. |
| 5,674,266 A | 10/1997 | Stendahl |
| 5,733,310 A | 3/1998 | Lopin et al. |
| 5,873,893 A | 2/1999 | Sullivan et al. |
| 5,879,374 A | 3/1999 | Powers et al. |
| 6,175,765 B1 | 1/2001 | Sullivan et al. |
| 6,185,458 B1 | 2/2001 | Ochs et al. |
| 6,208,895 B1 | 3/2001 | Sullivan et al. |

FOREIGN PATENT DOCUMENTS

| | | |
|---|---|---|
| EP | 0 553 864 A2 | 8/1993 |
| EP | 0 747 093 A2 | 12/1996 |
| WO | WO 93/16759 | 9/1993 |
| WO | WO 94/27674 | 12/1994 |
| WO | WO 95/05215 | 2/1995 |
| WO | WO 95/09673 | 4/1995 |
| WO | WO 98/39060 | 9/1998 |
| WO | WO 98/39061 | 9/1998 |

OTHER PUBLICATIONS

G.H. Bardy et al., "Trucated Biphasic Pulses for Transthoracic Defibrillation," *Circulation* 91(6):1768-1774, Mar. 15, 1995.

R.O. Cummins et al., Overview, "Ventricular Fibrillation, Automatic External Defibrillators, and the United Stated Food and Drug Administration: Confrontation Without Comprehension," *Annals of Emergency Medicine* 26(5):621,631, Nov. 1995.

S.A. Feeser et al., Abstract, "Strength-Duration and Probability of Success Curves of Defibrillation With Biphasic Waveforms," *Circulation* 82:2128, 1990.

B.E. Gliner et al., "Transthoracic Defibrillation of Swine with Monophasic and Biphasic Waveforms," *Circulation* 92(6):1634-1636, and 1638-1643, Sep. 15, 1995.

Kroll, M.W., "A Minimal Model of the Single Capacitor Biphasic Defibrillation Waveform," *PACE* 17(1):1782-1792, Nov. 1994.

A.S.L. Tang et al., Abstract, "Ventricular Defibrillation Using Biphasic Waveforms: The Importance of Phasic Duration," *Journal of American College of Cardiology* 13(1):207, Jan. 1989.

G.P. Walcott et al., "Choosing the Optimal Monophasic and Biphasic Waveforms for Ventricular Defibrillation," *Journal of Cardiovascular Electrophysiology* 6(9):737-750, Sep. 1995.

"Defibrillator," A Russian defibrillator manual (in English), 1993.

"Portable Defibrillator With General-Purpose Power Supply," an advertising brochure for a Russian defibrillator (in Russian and English), 1994, 4 pages.

METHOD FOR SELF-TEST OF DEFIBRILLATION AND PACING CIRCUITS INCLUDING A PATIENT ISOLATION SWITCH

CROSS-REFERENCE TO RELATED APPLICATION

This application is a continuation-in-part of U.S. patent application Ser. No. 10/096,408, filed Mar. 11, 2002, now U.S. Pat. No. 6,965,796, priority from the filing date of which is hereby claimed under 35 U.S.C. § 120.

FIELD OF THE INVENTION

This invention relates generally to methods and apparatus for self-tests in external defibrillators, and more particularly to a method and apparatus for verifying the integrity of defibrillation and pacing circuits including an isolation switch.

BACKGROUND OF THE INVENTION

One of the most common and life-threatening medical conditions is ventricular fibrillation, a condition where the human heart is unable to pump the volume of blood required by the human body. The usual way of restoring a normal rhythm to a heart experiencing ventricular fibrillation is to apply a strong electric pulse to the heart using an external cardiac defibrillator. External cardiac defibrillators have been successfully used for many years in hospitals by doctors and nurses, and in the field by emergency treatment personnel, e.g., paramedics.

Conventional external cardiac defibrillators first accumulate a high-energy electric charge on an energy storage capacitor. When a series of switching mechanisms are closed, the stored energy is transferred to a patient in the form of a large current pulse. The current pulse is applied to the patient via a pair of electrodes positioned on the patient's chest. A discharge control signal causes the series of switching mechanisms to complete an electrical circuit between the storage capacitor and a wave shaping circuit whose output is connected to the electrodes attached to the patient.

The series of switching mechanisms which couple the energy storage capacitor to the output of the defibrillator may be of different types and configurations. For example, in certain conventional biphasic defibrillators, the series of switching mechanisms may include an output circuit and an isolation relay. The output circuit may consist of a series of solid-state switches in an H-bridge configuration. The isolation relay may be a mechanical relay coupled between the output circuit and the patient, the purpose of which is to ensure that the patient is isolated from the defibrillation circuitry when energy is not being applied to the patient.

Existing self-test methods for defibrillation and pacing circuits verify the integrity of the output circuit while the isolation relay is in a nonconductive state. During these tests, the patient isolation relay is not activated so as to avoid the risk of shock to a patient or bystander. However, this also means that these tests do not verify the integrity of the patient isolation relay. The present invention is directed to a method and apparatus for performing self-tests on defibrillation and pacing circuits, and for verifying the integrity of the patient isolation relay.

SUMMARY OF THE INVENTION

A method and apparatus for performing self-tests on defibrillation and pacing circuits including a patient isolation switch is disclosed. In accordance with one aspect of the invention, the defibrillator output circuit is tested first, followed by a test of the pacing circuit, and finally a test of the isolation switch. Prior to the test of the isolation switch, the load impedance of the defibrillator is measured. If the impedance is in the range of a patient (e.g., 15 to 400 ohms), the test is aborted.

In accordance with another aspect of the invention, the test of the isolation switch will be performed differently depending on whether the load impedance of the defibrillator is determined to be a short circuit or an open circuit. If the load impedance is a short circuit, the test will attempt to conduct current through the 0 ohm load. If the load impedance is an open circuit, an alternate version of the test is performed that detects a DC offset voltage across the terminals of a preamp.

In accordance with yet another aspect of the invention, in an embodiment where the output circuit of the defibrillator is an H-bridge, the short-circuit test for the isolation switch includes the following steps. The NW and SE switches of the H-bridge are activated for a short time with the isolation switch inactive. If the processor detects nearly constant voltage on the energy storage capacitor, the isolation switch is open as expected. The isolation switch is then activated and the NW and SE switches of the H-bridge are again activated. If the voltage on the energy storage capacitor rapidly drops to a low level, the relay is conducting and is operational.

In accordance with still another aspect of the invention, in an embodiment where the output circuit of the defibrillator is an H-bridge, the open-circuit test for the isolation switch is performed according to the following steps. The NW and SE switches of the H-bridge are activated for a short time with the isolation switch inactive. The DC offset voltage across the preamp is compared to the level prior to activating the switches. If the voltage is relatively constant, the isolation switch is open, as expected. The isolation switch is then activated and the NW and SE switches of the H-bridge are again activated. If the DC offset voltage across the preamp increases to a high level, the relay is conducting and is operational. A similar test may be performed utilizing the impedance channel of the preamplifier as the test stimulus rather than using the voltage on the energy storage capacitor to provide the test stimulus. This same type of test stimulus can also be used to test the switches of the H-bridge output circuit, again in contrast to utilizing the voltage on the energy storage capacitor as the test stimulus. Not requiring the energy storage capacitor to be charged and discharged as part of the testing process conserves energy. Self-tests are also provided for the impedance drive circuits and the paddles preamplifier.

In accordance with yet another aspect of the invention, safety to a patient and bystanders is assured by adhering to the following protocols. The isolation test is only executed when turned on by an alarm (e.g., a real time clock alarm), as opposed to being activated by a user. Also, the test should only be performed when the impedance across the patient terminals is a short or open circuit, and not when the impedance is in the range of a human body. Finally, the test should not be performed if the voltage on the energy storage capacitor exceeds safe handling levels.

In accordance with still another aspect of the invention, the pacer circuitry of the present invention can be tested using a portion of the defibrillation circuit, such as one of the H-bridge switches, and does not need a test load, either internal or external. In addition, a pacing switch is isolated from the defibrillation circuits by a pacer relay. The pacer switch can be tested by monitoring the pace current or capacitor voltage with the pacer relay activated, then non-activated.

It will be appreciated that the disclosed method and apparatus for a self-test of defibrillation and pacing circuitry including an isolation switch is advantageous in that it allows the integrity of the isolation switch to be verified in addition to the integrity of the defibrillation and pacing circuitry.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
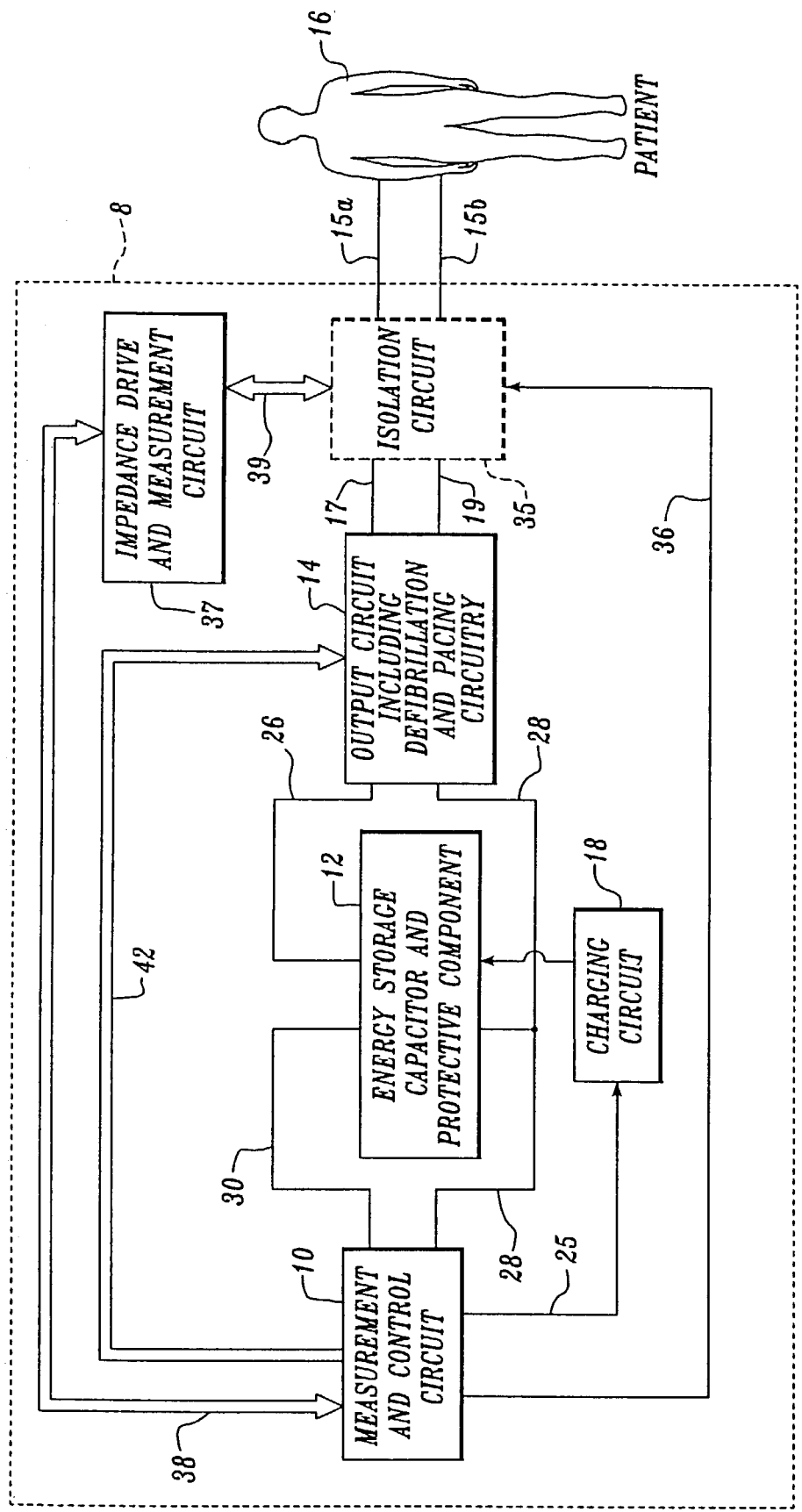
FIG. 1 is a block diagram of an external defibrillator having an output circuit and an isolation circuit.

FIG. 1 is a block diagram of an external defibrillator 8 that is connected to a patient 16. The defibrillator includes a measurement and control circuit 10 that is connected to an energy storage capacitor and protective component 12 via a charging circuit 18. During the operation of the defibrillator, the measurement and control circuit 10 controls the charging circuit 18 via a control line 25 to charge the energy storage capacitor to a desired voltage level. Feedback on the voltage level of the energy storage capacitor is provided to the measurement and control circuit 10 on a pair of lines 28 and 30.

After charging to a desired level, the energy stored in the energy storage capacitor may be delivered to the patient 16 in the form of a defibrillation pulse. The energy storage capacitor and protective component 12 is connected by lines 26 and 28 to an output circuit 14. Output circuit 14 includes defibrillation and pacing circuitry. The measurement and control circuit 10 is connected to the output circuit 14 by a control bus 42 and to an isolation circuit 35 by a control line 36. Application of appropriate control signals over the control bus 42 and control line 36 causes the output circuit 14 to conduct energy from the energy storage capacitor. The energy is delivered to the patient 16 attached to the defibrillator 8 over a set of electrodes 15A and 15B. The electrode 15A is attached to an apex line 17 in output circuit 14 through the isolation circuit 35. The electrode 15B is attached to a sternum line 19 in output circuit 14 through the isolation circuit 35.

The measurement and control circuit 10 also controls and receives measurements through a bus line 38 from an impedance drive and measurement circuit 37. The impedance drive and measurement circuit 37 is coupled to the isolation circuit 35 through a bus line 39. The impedance drive and measurement circuit 37 provides measurements of the impedance of the patient 16.

Figure 2:
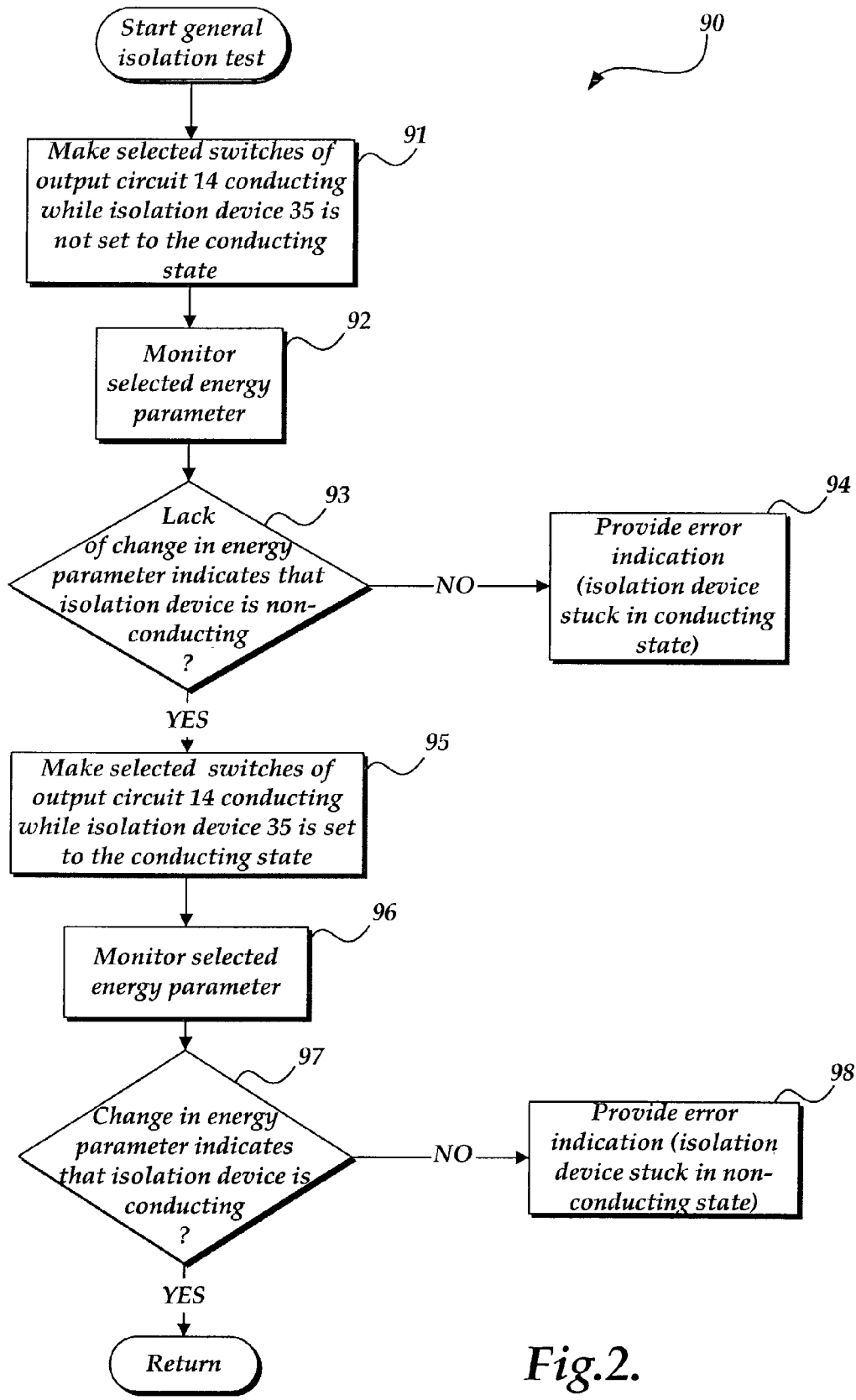
FIG. 2 is a flow diagram illustrating a general self-test for an isolation switch.

FIG. 2 is a flow chart of a general self-test 90 for the isolation circuit 35. A more specific self-test for an isolation circuit in a defibrillator with an H-bridge output circuit is described in more detail below with reference to FIGS. 7–9. As shown in FIG. 2, at a block 91, the routine makes selected output circuit switches (e.g., switches of the output circuit 14 of FIG. 1) conducting while the isolation device (e.g., isolation circuit 35) is not set to the conducting state. At a block 92, a selected energy parameter is monitored. It will be understood that the monitoring of the selected energy parameter may be done during the operation at block 91.

At a block 93, the routine determines whether the energy parameter has changed. In general, if the energy parameter has not changed, it indicates that the isolation device is indeed in the nonconducting state, as expected. On the other hand, a change in the energy parameter indicates that the isolation device may be stuck in a conducting state. Thus, from decision block 93, if there is not a lack of change in the energy parameter (i.e., the energy parameter has changed), the routine proceeds to a block 94, where an error indication is provided, as the isolation device may be stuck in a conducting state.

From block 93, if there is a lack of change in the energy parameter (i.e., the energy parameter has not changed), then the isolation device appears to be nonconducting as expected, and the routine proceeds to a block 95. At block 95, the routine makes selected output circuit switches conducting while the isolation device is set to the conducting state. At a block 96, the selected energy parameter is monitored. As noted above, the monitoring of the selected energy parameter may take place during the operation at block 95.

At a decision block 97, the routine determines whether the energy parameter has changed. If there is not a change in the energy parameter, then the routine proceeds to a block 98 where an error indication is provided, as the isolation device appears to be stuck in a nonconducting state. If there is a change in the energy parameter, then the isolation device appears to be functioning properly, and the routine returns.

Figure 3A:
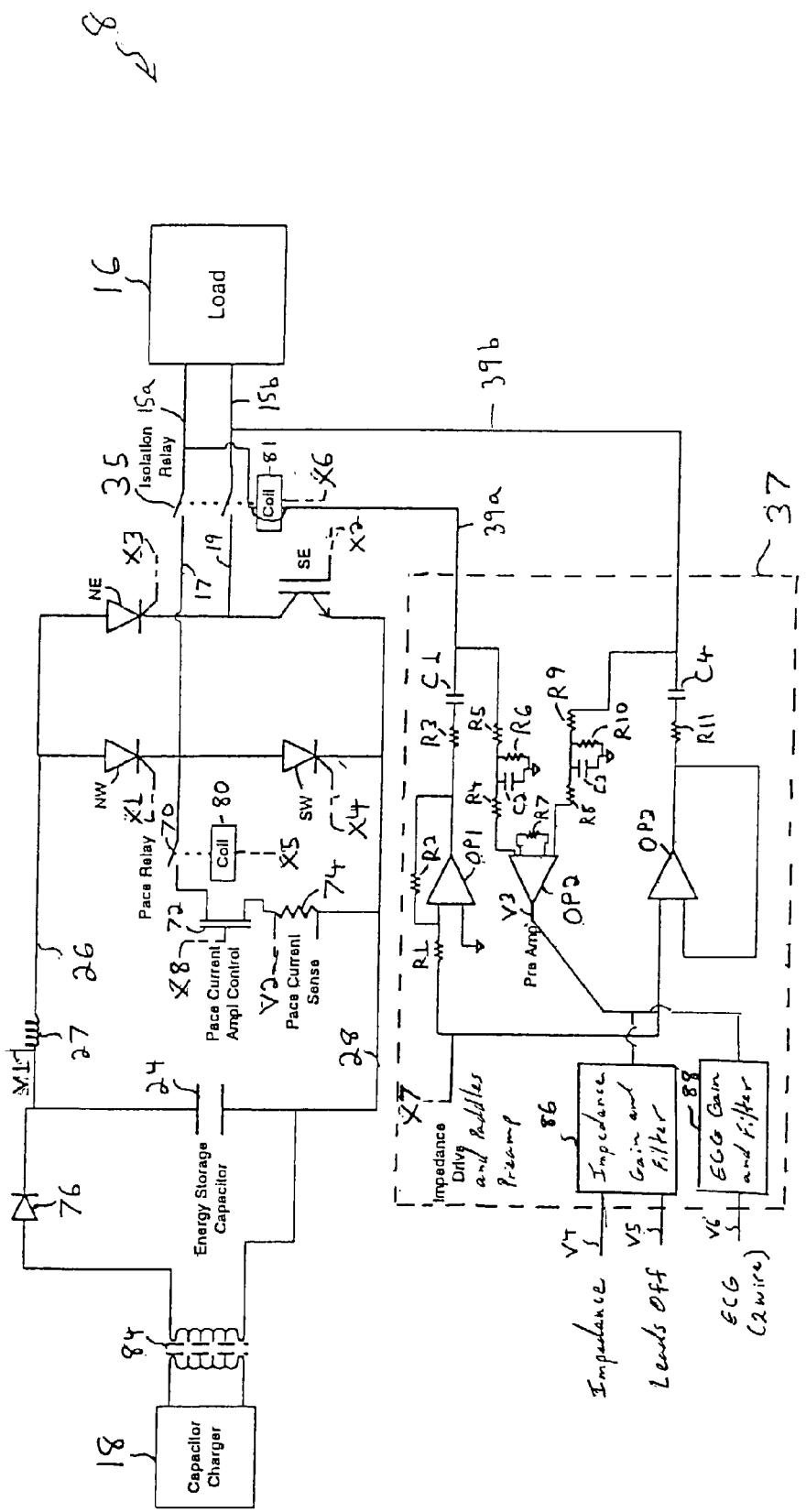
FIGS. 3A and 3B are schematic diagrams of a biphasic defibrillator including defibrillation and pacing circuitry and an isolation switch.
Figure 3B:
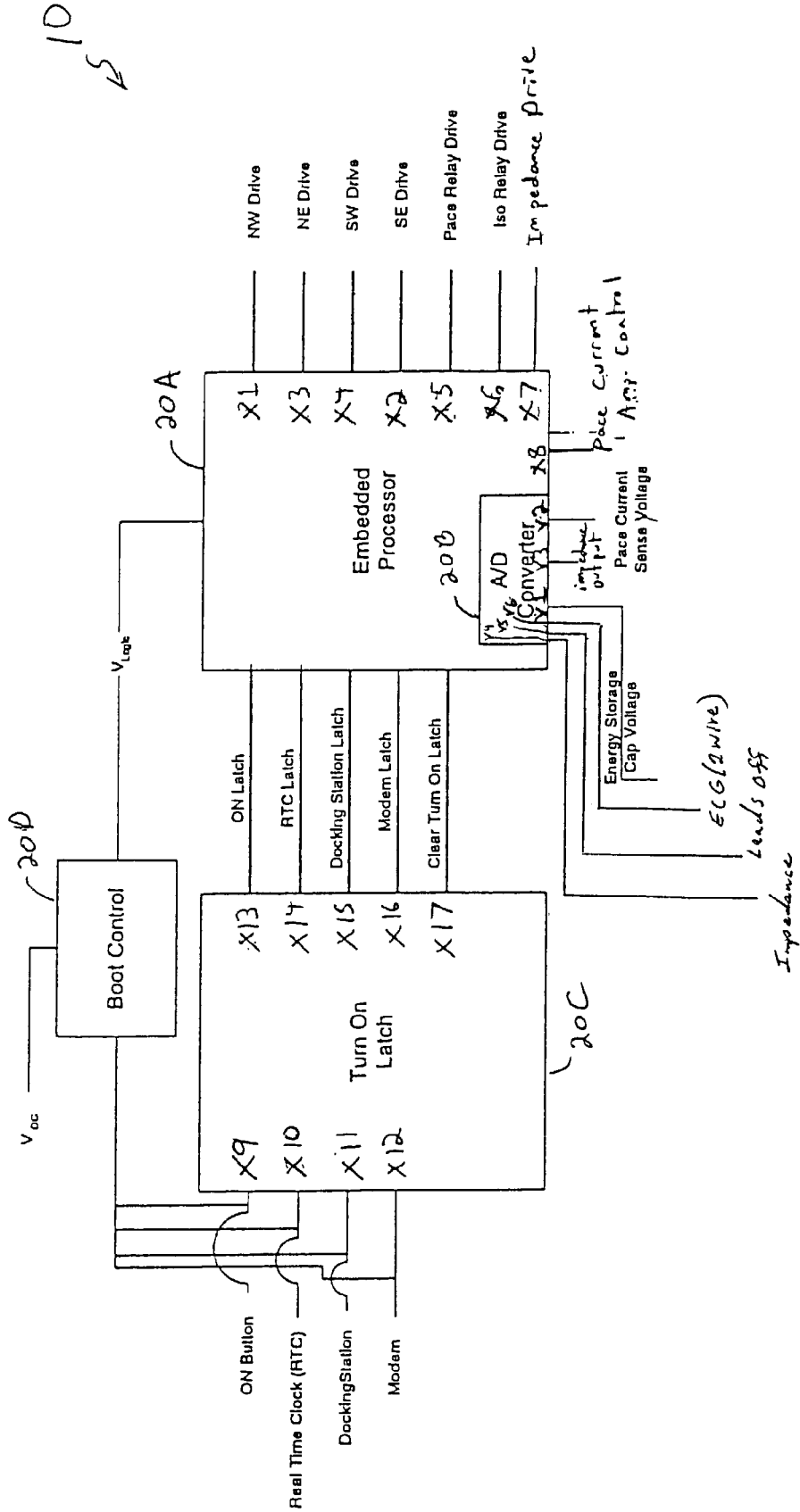

FIGS. 3A and 3B are schematic diagrams of a defibrillator 8 including defibrillation and pacing circuitry, along with an isolation relay. A defibrillator with a similar H-bridge output circuit, along with certain exemplary self-test methods, are described in copending U.S. patent application Ser. No. 09/706,578, entitled "H-Bridge Circuit for Generating a High-Energy Biphasic Waveform in an External Defibrillator," and in U.S. Pat. No. 5,873,893, which are each commonly assigned and which are each hereby incorporated by reference in their entireties. As shown in FIG. 3A, four output switches NW, SE, NE, and SW are in the form of an H-bridge and allow the transfer of energy from the energy storage capacitor 24 on lines 26 and 28. Switches NW, NE, and SW are semiconductor switches, preferably silicon controlled rectifiers (SCRs). Switch SE is an insulated gate bipolar transistor (IGBT). The four output switches NW, SE, NE, and SW can be switched from an off (nonconducting) to an on (conducting) condition. Control lines X1, X2, X3, and X4 are controlled from an embedded processor 20A (FIG. 3B), to control the output switches NW, SE, NE, and SW, respectively.

Each of the four switches NW, SE, NE, and SW form one leg of an H-bridge output circuit. Switches NW and NE are coupled through a protective component 27 to the positive lead of the energy storage capacitor 24 by a bridge line 26. The switches SW and SE are coupled to the negative lead of the energy storage capacitor 24 by a bridge line 28. The center cross-line of the H-bridge includes the load 16 (e.g., the patient, when connected). The load 16 is connected to the left side of the bridge by an electrode 15A that is coupled through the isolation relay 35 to an apex line 17. The load 16 is coupled to the right side of the bridge by an electrode 15B through the isolation relay 35 to a sternum line 19. The isolation relay 35 is controlled by a coil 81, which receives a control signal line X6 from the embedded processor 20A (FIG. 3B).

The defibrillator also includes pacing circuitry, including a pace relay 70, a pace current transistor 72, and a pace current sense resistor 74. A defibrillator with similar pacing circuitry is described in U.S. Pat. No. 6,208,895, which is commonly assigned and hereby incorporated by reference in its entirety. The pace relay 70, the pace current transistor 72, and the pace current sense resistor 74 are coupled in series between the apex line 17 and the bridge line 28. The pace relay 70 is controlled by a coil 80 that receives a control line X5 from the embedded processor 20A (FIG. 3B). The pace current transistor 72 provides amplitude control for the pacing circuitry and is controlled by a control line X8 from the embedded processor 20A (FIG. 3A). The pace current sense resistor 74 includes a signal line (or lines) for providing a voltage line V2 that indicates the current through the pacing circuitry.

A capacitor charger 18 is coupled through an isolating transformer 84 to the energy storage capacitor 24. A rectifying diode 76 is coupled between the isolating transformer 84 and the positive lead of the energy storage capacitor 24. The voltage on the energy storage capacitor is provided through a voltage line V1 to an A-to-D converter 20B in the embedded processor 20A (FIG. 3B).

The defibrillator 8 also includes impedance drive and measurement circuitry 37. The impedance drive and measurement circuit 37 is coupled through lines 39A and 39B to the electrodes 15A and 15B, respectively. The impedance drive and measurement circuit 37 also receives an impedance drive control line X7 from the embedded processor 20A, and provides an output signal line V3 to the A-to-D converter 20B of the embedded processor 20A (FIG. 3A).

In the impedance drive and measurement circuit 37, the impedance drive control line X7 is coupled through a resistor R1 to a first input of an operational amplifier OP1. The second input of the operational amplifier OP1 is coupled to ground. The first input of the operational amplifier OP1 is coupled through a resistor R2 to the output of the operational amplifier OP1. The output of the operational amplifier OP1 is coupled through a resistor R3 and a capacitor C1 in series to the electrode 15A. The electrode 15A is coupled through a resistor R5 and the resistor R4 in series to a first input of an operational amplifier OP2. Second and third inputs of the operational amplifier OP2 are connected together through a resistor R7. The circuit node between resistors R4 and R5 is connected through a capacitor C2 and a resistor R6 in parallel to ground. The fourth input of the operational amplifier OP2 is connected through a resistor R8 and a resistor R9 in series to the electrode 15B. The node between the resistors R4 and R9 is coupled through a capacitor C3 and a resistor R10 in parallel to ground. The output of the operational amplifier OP2 provides the signal line V3 (i.e., the preamp signal). The signal line V3 is coupled to an impedance and gain filter 86 which produces an impedance signal V4 and a leads off signal V5. The signal line V3 is also coupled to an ECG gain and filter 88 which produces an ECG 2-wire signal V6. Thus, the output V3 of the instrumentation amplifier OP2 is processed for impedance information by high frequency filter and gain stages and for ECG signals by low frequency filter and gain stages. Electrode 15B is coupled through a capacitor C4 and a resistor R11 in series to the output of an operational amplifier OP3. A first input of the operational amplifier OP3 receives the control signal X7, while the second input of the operational amplifier OP3 is coupled to the output of the operational amplifier OP3.

FIG. 3B shows the measurement and control circuitry for the defibrillator of FIG. 3A. As shown, the measurement and control circuitry 10 includes an embedded processor 20A, a turn-on latch 20C, and a boot control 20D. The A-to-D converter 20B is included within the embedded processor 20A. The embedded processor 20A provides control signal line X1 which controls the switch NW, control signal line X2 which controls the switch SE, control signal line X3 which controls the switch NE, control signal line X4 which controls the switch SW, control signal line X5 which controls the pace relay drive, control signal line X6 which controls the isolation relay drive, control signal line X7 which controls the impedance drive, and control signal line X8 which provides the pace current amplitude control.

The A-to-D converter 20B of the embedded processor 20A receives voltage signal line V1 which indicates the voltage on the energy storage capacitor, a voltage signal line V2 which indicates the pace current sense voltage, a voltage signal line V3 which indicates the output of the impedance drive, a voltage signal line V4 which indicates an impedance measurement, a voltage signal line V5 which indicates a leads off signal, and a voltage signal line V6 which indicates an ECG 2-wire signal. The embedded processor 20A is coupled to the turn-on latch 20C by five signal lines, including the signal line X13 for the on latch, the signal line X14 for the real time clock (RTC) latch, the signal line X15 for the docking station latch, the signal line X16 for the modem latch, and the signal line X17 for the clear turn-on latch. The embedded processor 20A is also coupled to the boot control 20D by a voltage signal line Vlogic. The turn-on latch 20C also receives a signal line X9 from the on button, a signal line X10 from the real time clock (RTC), a signal line X11 from the docking station, and a signal line X12 from the modem. The signal lines X9–X12 are also coupled to the boot control 20D. Boot control 20D also receives a voltage signal VDC.

The imbedded processor 20A controls the switches NW, SE, NE, and SW for the H-bridge, the pacing relay 70, the pace current amplitude control transistor 72, and the isolation relay coil 81. The processor 20A also monitors the voltage on the energy storage capacitor through the signal line V1, and the pace current sense voltage on the signal line V2.

As described above, the turn-on latch 20C is connected to several turn-on switches and thus receives control signals from an on button on the signal line X9, and from a wake-up device for signaling periodic self-test on the signal line X10. The wake-up device for signaling periodic self-tests is designated as a real time clock (RTC). After booting or while operating, the processor 20A can read and then clear each latch.

The impedance drive circuit 37 generates a low-level (safe) AC signal across a patient 16 connected to the terminals through electrodes 15A and 15B. The amplitude of the impedance signal at the input to the preamp of circuit 37 will change with the load impedance. The preamp of circuit 37 is capable of measuring low frequency patient ECG signals as well as the impedance drive signal.

When not in use, the design of the defibrillator will provide either a 0 ohm or an open circuit across the output terminals where the electrodes 15A and 15B are coupled. The preamp impedance measurement circuit 37 has sufficient resolution to detect either of these load values in addition to expected patient impedance values. (e.g., 15 to 400 ohms).

Defibrillator 8 of FIGS. 3A and 3B provides a biphasic defibrillation pulse to the load 16 (e.g., the patient) in the following manner. Once the energy storage capacitor 24 is charged to a selected energy level and the patient isolation relay 35 is closed, the switches NW and SE are switched on so as to provide a path from the energy storage capacitor to apex line 17 and sternum line 19, respectively, for the application of a first phase of a defibrillation pulse to the patient. The stored energy travels from the positive terminal of the capacitor 24 on line 26, through switch NW, across apex line 17, across the patient 16, back across sternum line 19, and through switch SE to the negative terminal of the capacitor 24 on line 28. The first phase of the biphasic pulse therefore applies a positive pulse from the apex to the sternum of the patient.

Before the energy storage capacitor 24 is completely discharged, switch SE is biased off in preparation for applying the second phase of the biphasic pulse. Once switch SE is biased off, switch NW will also become nonconducting because the current through the SCR falls to zero.

After the end of the first phase of the biphasic defibrillation pulse, the switches NE and SW are switched on to start the second phase of the biphasic pulse. Switches NE and SW provide a path to apply a negative defibrillation pulse to the patient. With reference to FIG. 3A, the energy travels from the positive terminal of the capacitor 24 on line 26, through switch NE, across sternum line 19, through the patient 16, back across apex line 17, and out through switch SW to the negative terminal of the capacitor 24 on line 28. The polarity of the second phase of the defibrillation pulse is therefore opposite in polarity to the first phase of the pulse. The end of the second phase of the biphasic pulse is truncated by switching on switch NW to provide a shorted path for the remainder of the capacitor energy through switches NW and SW. After the second phase is truncated, all four of the switches NW, SE, NE, and SW are switched off. The patient isolation relay 35 is also opened in preparation for providing another defibrillation pulse.

Figure 4:
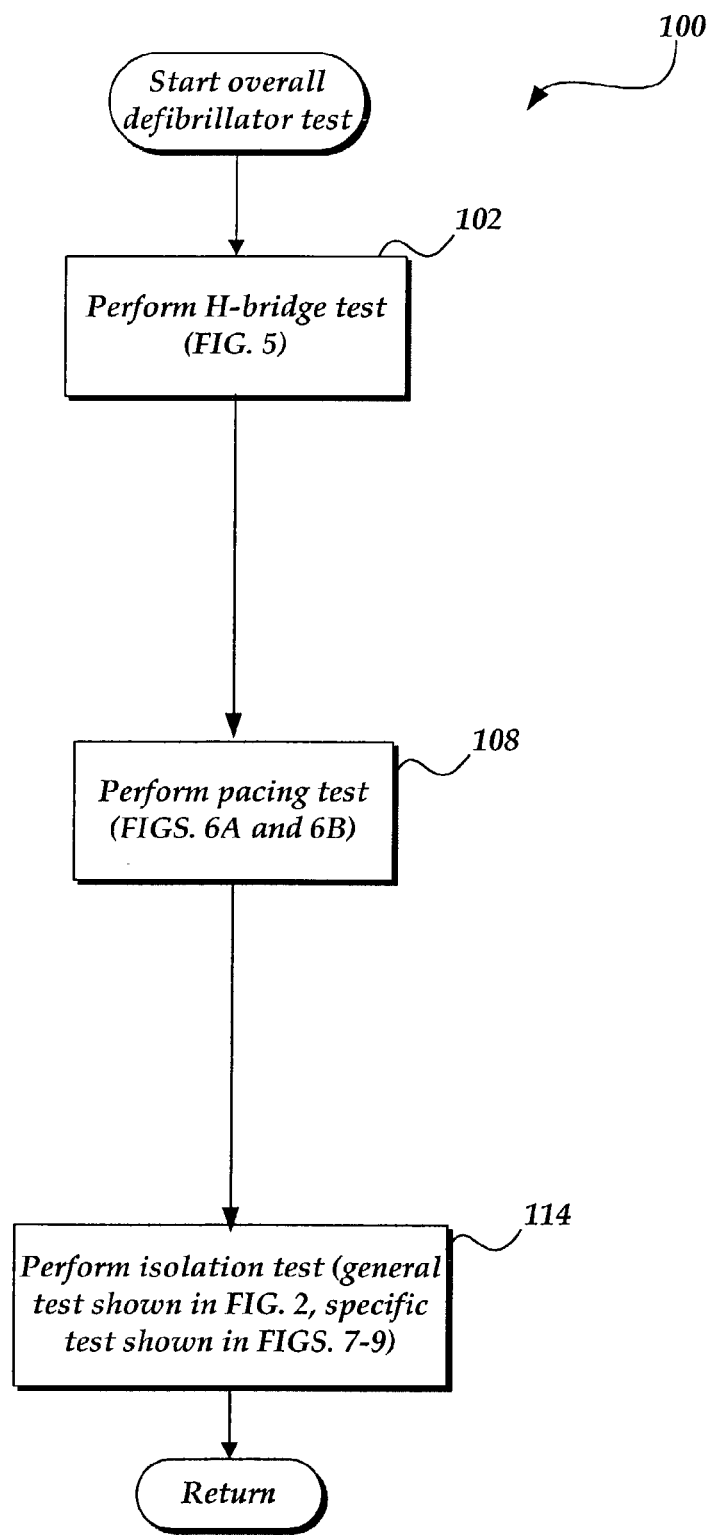
FIG. 4 is a flow diagram illustrating an overall self-test for a defibrillator.

FIG. 4 illustrates an overall defibrillator test 100. At a block 102, an H-bridge test is performed (as will be described in more detail below with reference to FIG. 5). Then, at a block 108, a pacing test is performed (as will be described in more detail below with reference to FIGS. 6A and 6B). Finally, at block 114, an isolation test is performed (as was generally described above with reference to FIG. 2, and as will be described in more detail below with references to FIGS. 7 to 9).

Figure 5:
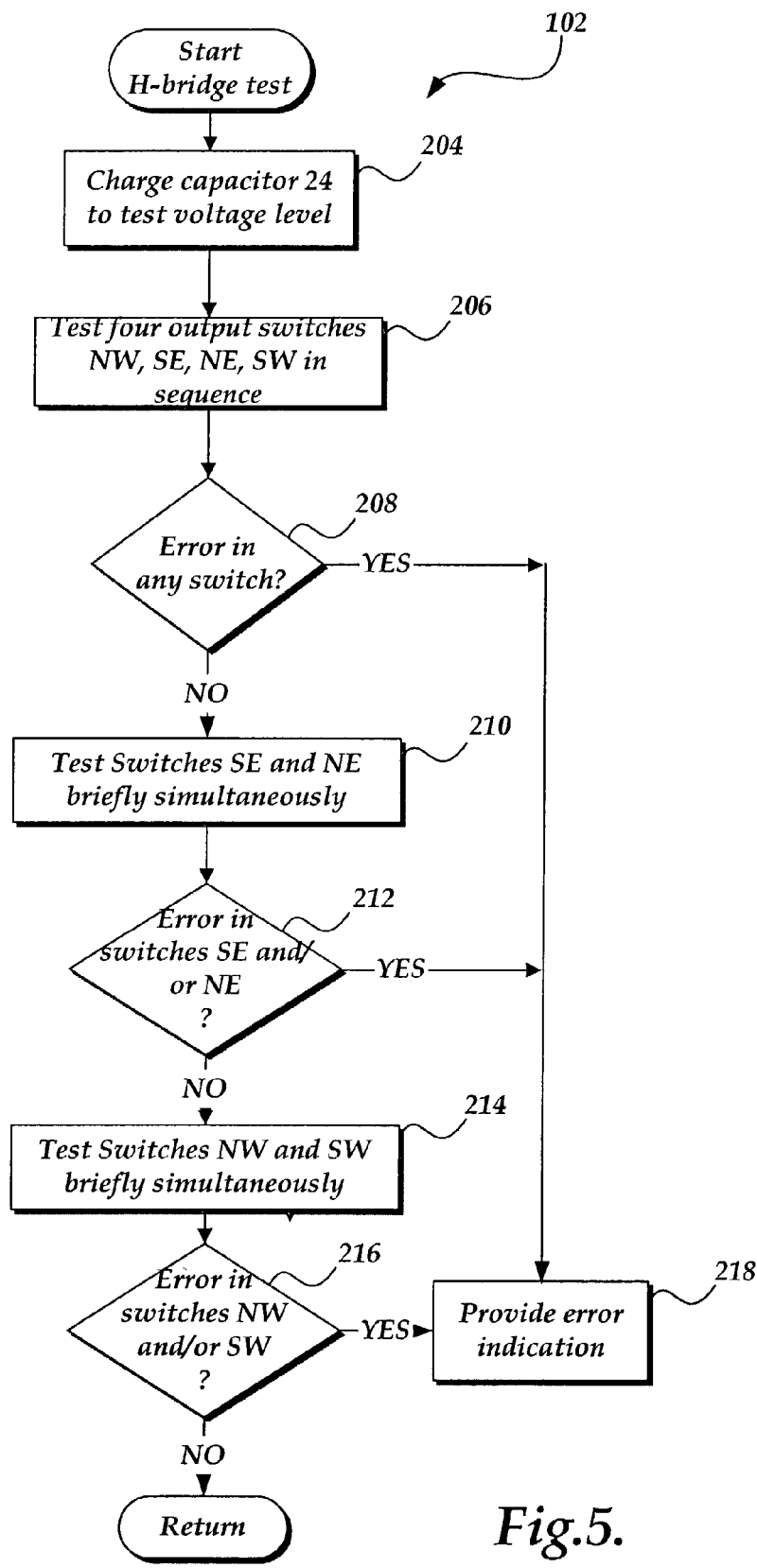
FIG. 5 is a flow diagram illustrating a self-test for an H-bridge.

FIG. 5 shows a self-test 102 for verifying the integrity of the H-bridge. The energy storage capacitor 24 is charged to a test voltage at a block 204. The test voltage to which the energy storage capacitor is charged may be less than the maximum allowed voltage of the capacitor if energy conservation during the start-up test is desired. A lower voltage requires less charging time, and therefore allows the total start-up test time of the output circuit to be shortened. The test voltage should be high enough, however, to allow a reasonable test of the integrity of the output switches NW, SE, NE and SW, as set forth below. During the entirety of the self-test of the output circuit, it will be appreciated that the patient isolation relay 35 is opened to prevent any current from flowing to a patient.

After charging the energy storage capacitor 24, at a block 206 a sequential test is made of the four output switches NW, SE, NE and SW. The output switches are initially tested by switching the switches off. After placing each of the switches in the nonconducting state, each switch is individually switched on and then off again in sequence. That is, the first switch NW is switched on and then off, followed by the remaining switches in turn. As the switches are being switched on and off, the voltage level across the energy storage capacitor is monitored. No change in the voltage level across the energy storage capacitor 24 should occur during the tests, because switching on a single switch does not provide a conductive path through the output circuit that would allow the energy stored in the energy storage capacitor to discharge. If any change in the voltage level across the capacitor during the sequential switching on and off of switches NW, SE, NE and SW is detected, an error is indicated. At a block 208, a test is made to determine whether there were errors detected in any of the switches NW, SE, NE and SW. If any errors were detected in the switches, at a block 218 an error indication is provided. If no errors were detected in the switches, the routine proceeds to a block 210.

At block 210 the switches SE and NE are tested simultaneously for a brief interval. The two switches are tested by simultaneously switching on both switches SE and NE. The switches are turned off by biasing switch SE off, which causes switch NE to become nonconducting since it is an SCR. When switches SE and NE are simultaneously conducting, a drop in the voltage across the energy storage capacitor should be detected due to the shorted path that is provided through the output circuit. If a voltage drop is not detected when switches SE and NE are supposed to be simultaneously conducting, then an error is indicated. At a block 212, a test is made to determine whether an error was detected in the combination of switches SE and NE. If an error was detected, the routine continues to the error indication routine at block 218. If no error was detected in switches SE and NE, the routine continues to a block 214.

At block 214, a test is made of switches NW and SW. Switches NW and SW are tested by simultaneously switching the switches on. Switching on switches NW and SW causes a conductive path to be created from the energy storage capacitor 24 through the output circuit. A voltage drop across the energy storage capacitor should therefore be detected. If a voltage drop is not detected when switches NW and SW are simultaneously switched on, then an error is indicated. At block 216, a test is made to determine whether an error was detected in the combination of switches NW and SW. If an error was detected, the routine continues to the error indication routine at block 218. If no error was detected in switches NW and SW, the H-bridge test returns.

It will be appreciated that in the embodiment of the output circuit described above, the set of switches SE and NE must be tested before the set of switches NW and SW. If switches NW and SW had been tested first, it would have been impossible to switch the switches NW and SW off while current was flowing through them because they are both SCR devices. Testing switches NW and SW first would therefore have drained all the test energy from the energy storage capacitor 24. Because switch SE is an IGBT that can be made nonconducting, the combination of switches SE and NE can be switched off. Testing the switches in the correct order therefore allows the energy storage capacitor to be charged a single time in order to test all four switches. It will be appreciated, however, that a different switch testing order could be used if the capacitor were recharged or if different switches were used in the output circuit.

The self-test for the H-bridge is often performed immediately after turning the defibrillator on because it requires extra time and energy to charge and then dissipate the energy in the energy storage capacitor. The amount of time and energy that the self-test for the H-bridge takes can be varied by changing the voltage level to which the energy storage capacitor is charged. Using a lower voltage level reduces the charge time of the capacitor. In an alternate embodiment, a "skip start-up test" button or command may also be incorporated in the defibrillator to allow a user to bypass the start-up verification test as the defibrillator is powered on.

In addition to being performed when a user powers on the defibrillator, in an alternate embodiment the self-test for the H-bridge may also be performed periodically by the embedded processor 20A while the defibrillator is not in use. For example, at a certain time each night, the embedded processor 20A could automatically and without user intervention power on the defibrillator, perform tests to verify the integrity of the circuitry and provide a warning signal to a user if a failure has occurred.

Figure 6A:
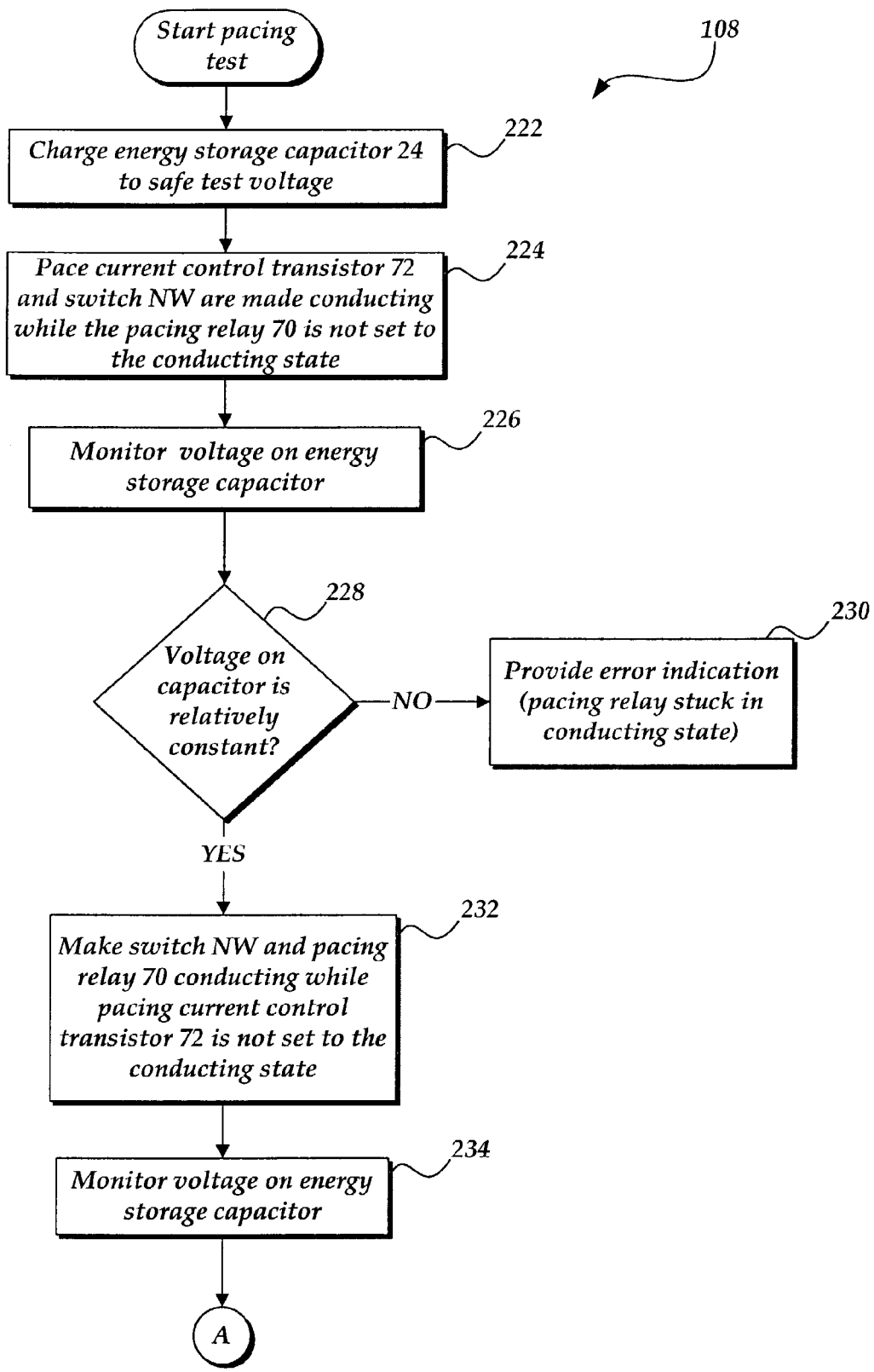
FIGS. 6A and 6B are flow diagrams illustrating a self-test for pacing circuitry.
Figure 6B:
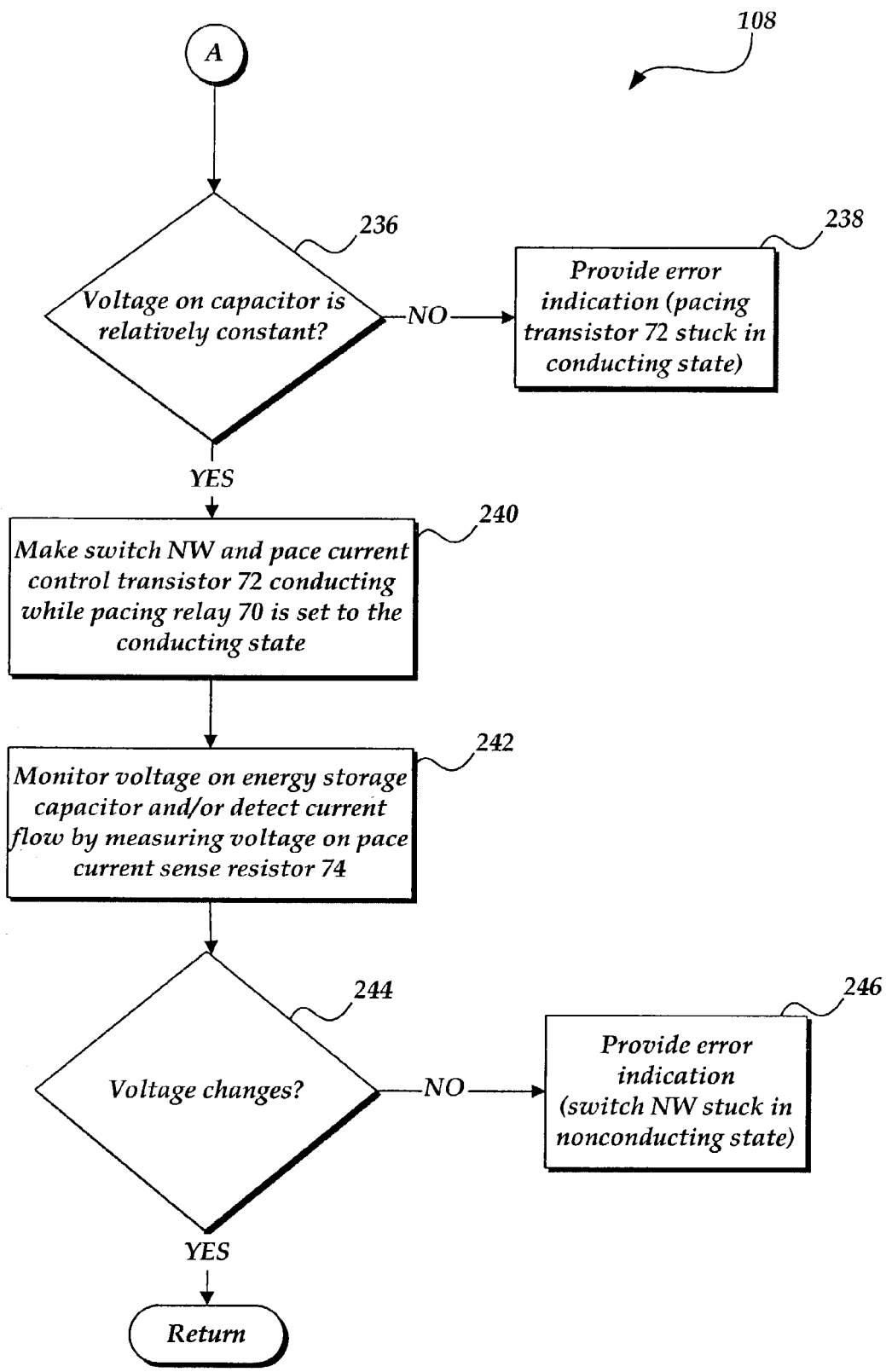

FIGS. 6A and 6B are flow diagrams of a self-test 108 for the pacing circuitry of the defibrillator 8 of FIG. 3A. As shown in FIG. 6A, at a block 222, the energy storage capacitor 24 is charged to a safe test voltage. At a block 224, the pace current control transistor 72 and the switch NW are made conducting while the pacing relay 70 is not set to the conducting state. At block 226, the voltage on the energy storage capacitor 24 is monitored. It will be understood that the monitoring of the voltage in block 226 may be performed during the procedure of the block 224.

At a decision block 228, the routine determines whether the voltage on the energy storage capacitor 24 is relatively constant. If the voltage on the energy storage capacitor is not relatively constant, the routine proceeds to a block 230, where an error indication is provided, as the pacing relay 70 may be stuck in a conducting state. If at the decision block 228 it is determined that the voltage on the energy storage capacitor 24 is relatively constant, then the routine proceeds to a block 232.

At block 232, the routine makes switch NW and pacing relay 70 conducting while the pacing current control transistor 72 is not set to a conducting state. At a block 234, the voltage on the energy storage capacitor is monitored. It will be appreciated that the monitoring of the voltage on the energy storage capacitor 24 at block 234 may be performed during the procedures of the block 232. The routine then proceeds to a decision block 236 of FIG. 6B.

As shown in FIG. 6B, at a decision block 236 the routine determines whether the voltage on the energy storage capacitor 24 is relatively constant. If the voltage on the energy storage capacitor 24 is not relatively constant, then the routine proceeds to a block 238 where an error indication is provided, as it appears that the pacing transistor 72 may be stuck in a conducting state. If at decision block 236 the voltage on the energy storage capacitor 24 is determined to be relatively constant, then the routine proceeds to a block 240.

At block 240, the routine makes the switch NW and the pace current control transistor 72 conducting while the pacing relay 70 is set to the conducting state. At a block 242, the voltage on the energy storage capacitor is monitored. It will be appreciated that current flow can also be detected by measuring the voltage on the pace current sense resistor 74. It will be further appreciated that the monitoring of the voltage on the energy storage capacitor block 242 may be performed during the procedures of the block 240.

At a decision block 244, the routine determines whether the voltage on the energy storage capacitor, and/or the current as determined by monitoring whether the voltage on the pace current sense resistor 74 changes. If the voltage does not change, the routine proceeds to a block 246, where an error indication is provided, as it appears that the switch NW may be stuck in a nonconducting state. If at block 244 the routine determines that the voltage does change, then the routine ends and returns.

It will be appreciated that the pacing circuitry of the present invention can be tested using a portion of the defibrillation circuit (i.e., switch NW) and does not require a test load (either internal or external). In addition, the pacer (i.e., pace current control transistor 72) is isolated from the defibrillation circuits by the pacer relay 70. The pace current control transistor 72 can be tested by monitoring the pace current, such as on line V2, or the capacitor voltage, such as on line V1, with the relay activated, then nonactivated.

As will be described in more detail below with reference to FIGS. 7–9, activation of the RTC alarm on signal line X10 is the trigger for the self-test. After booting, the processor 20A reads the latches, determines that boot up is due only to the RTC alarm, and initiates the RTC self-test. If the "on" button on signal line X9 is also pushed or is pushed at any time during the self-test, the processor 20A switches to normal operation mode. During the self-test, the preamp of the circuit 37 measures the load impedance. If the impedance is 0 ohms or an open circuit, then a patient or bystander is presumed to not be in contact with the patient terminals at the electrodes 15A and 15B, and the isolation test may be performed.

Figure 7:
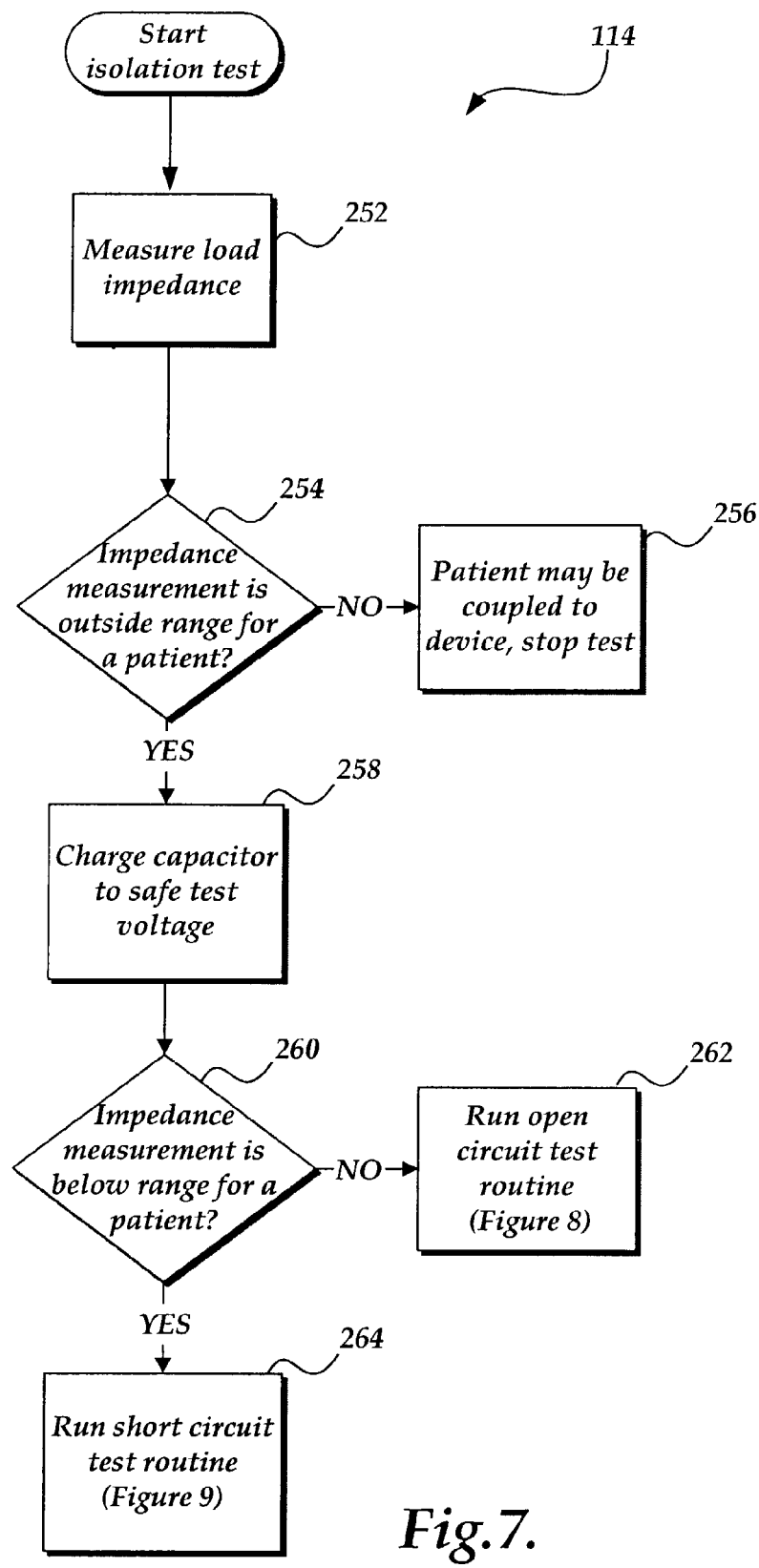
FIG. 7 is a flow diagram illustrating a self-test for an isolation switch.

FIG. 7 shows a flow diagram of a self-test 114 for the isolation relay 35 of FIG. 3A. At a block 252, the load impedance is measured by the preamp at signal line V3 from impedance circuit 37. At a block 254, the routine determines whether the impedance measurement is outside the range for a patient. In a preferred embodiment, a selected range for patient impedances is 15 to 400 ohms. If the impedance measurement is not outside the range for a patient, then the routine proceeds to a block 256, where the test is aborted, as the indication is that a patient may be coupled to the device. If at decision block 254 the impedance measurement is outside the range for a patient, thus indicating that the load is likely shorted or open, then the routine continues to a block 258.

At block 258, the energy storage capacitor 24 is charged to a safe test voltage. At a decision block 260, the routine determines whether the impedance measurement is below the range for a patient. If the impedance measurement is above the range for a patient, then the routine proceeds to block 262, where an open-circuit test routine is run, as will be described in more detail below with reference to FIG. 8. If at decision block 260 it is determined that the impedance measurement is below the range for a patient, then the routine proceeds to a block 264, where a short-circuit test routine is run, as will be described in more detail below with reference to FIG. 9.

Figure 8:
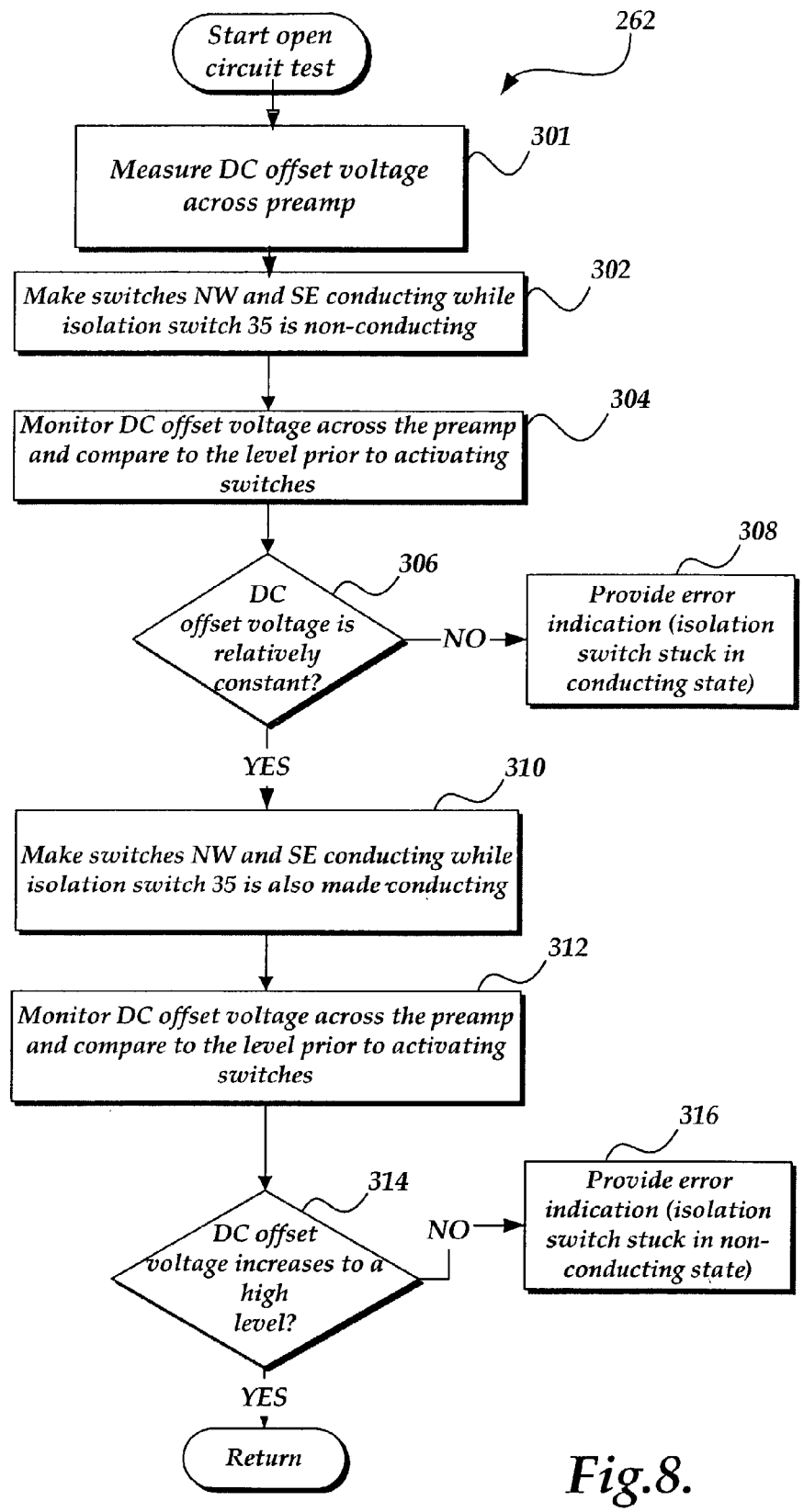
FIG. 8 is a flow diagram illustrating a self-test for an isolation switch when an open-circuit load impedance is detected.

FIG. 8 shows a flow diagram of a self-test 262 for the isolation switch 35 when an open circuit is detected for the load impedance. At a block 301, a DC offset voltage across the preamp of the impedance circuit 37 is measured. At a block 302, the switches NW and SE are made conducting while the isolation switch 35 is nonconducting. At a block 304, the DC offset voltage across the preamp is monitored and compared to the level prior to activating the switches at block 302. It will be appreciated that the monitoring of the DC offset voltage across the preamp at block 304 may be done during the activation of the switches at block 302.

At a decision block 306, the routine determines whether the DC offset voltage across the preamp was relatively constant. If the DC offset voltage across the preamp was not relatively constant, then the routine proceeds to a block 308, where an error indication is provided, as the indication is that the isolation switch may be stuck in a conducting state. If at decision block 306 it is determined that the DC offset voltage of the preamp was relatively constant, then the routine proceeds to a block 310.

At block 310, the routine makes the switches NW and SE conducting while the isolation switch 35 is also made conducting. At a block 312, the DC offset voltage across the preamp is monitored and compared to the level prior to activating the switches at block 310. It will be appreciated that the monitoring of the DC offset voltage at block 312 may be done during the activation of the switches at block 310.

At a decision block 314, the routine determines whether the DC offset voltage has increased to a high level. If the DC offset voltage has not increased to a high level, then the routine proceeds to a block 316 where an error indication is provided, as the indication is that the isolation switch is stuck in a nonconducting state. If at decision block 314 it is determined that the DC offset voltage has increased to a high level, then the indication is that the relay is conducting and operational, and the routine returns.

Figure 9:
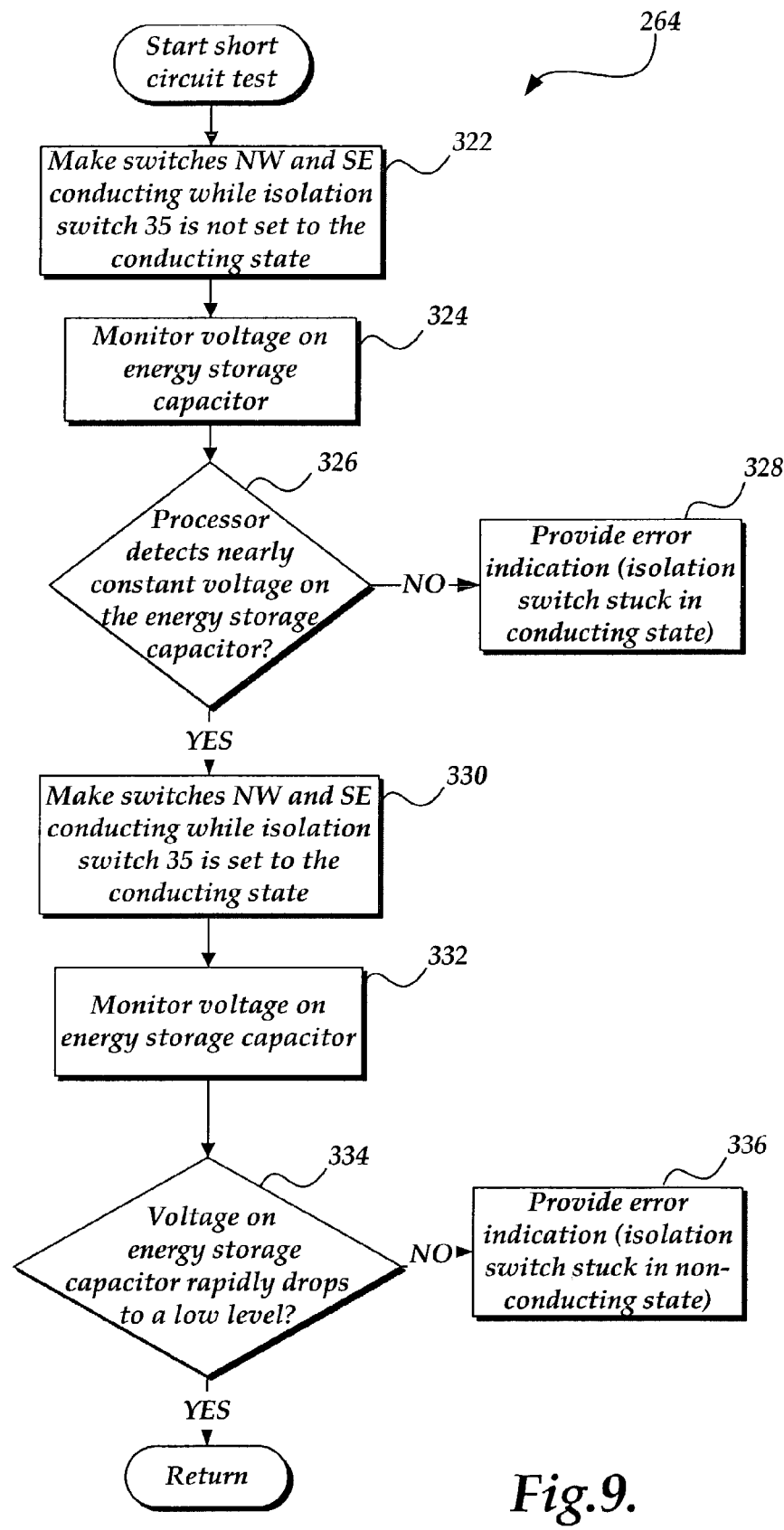
FIG. 9 is a flow diagram illustrating a self-test for an isolation switch when a short-circuit load impedance is detected.

FIG. 9 shows a flow diagram of a self-test 264 for the isolation switch 35 when a short circuit is detected for the load impedance. At a block 322, the switches NW and SE are made conducting while the isolation switch 35 is not set to the conducting state. At a block 324, the voltage on the energy storage capacitor is monitored. It will be appreciated that the monitoring of the voltage on the energy storage capacitor block 324 may be performed during the operations of block 322.

At a decision block 326, the routine determines whether the processor detected a nearly constant voltage on the energy storage capacitor. If there was not a nearly constant voltage on the energy storage capacitor, then the routine proceeds to a block 328, where an error indication is provided, as the indication is that the isolation switch may be stuck in a conducting state. If at decision block 326 it is determined that there was a nearly constant voltage on the energy storage capacitor, then the routine proceeds to a block 330.

At block 330, the routine makes the switches NW and SE conducting while the isolation switch 35 is set to the conducting state. At a block 332, the voltage on the energy storage capacitor is monitored. It will be appreciated that the monitoring of the voltage on the energy storage capacitor at block 332 may be performed during the operations at block 330.

At a decision block 334, the routine determines whether the voltage on the energy storage capacitor rapidly dropped to a low level. If the voltage on the energy storage capacitor did not rapidly drop to a low level, then the routine proceeds to a block 336 where an error indication is provided, as the indication may be that the isolation switch may be stuck in a nonconducting state. If at decision block 334 it is determined that the voltage on the energy storage capacitor did rapidly drop to a low level, then the indication is that the isolation switch is conducting and operational, and the routine returns.

FIGS. 7–9 above describe a self-test for verifying the integrity of the isolation switch. In a preferred embodiment, safety to a patient and bystanders during the self-test can be assured by following certain safety protocols. One of these protocols is to only execute the test when it is activated by the real time clock (RTC) alarm, as opposed to being activated by a user. Further, as noted at block 254 of FIG. 7, the test is only conducted if the impedance across the output terminals indicates a short circuit or an open circuit, as opposed to being in the range of a patient. In addition, at block 258 of FIG. 7, it is noted that the capacitor is only charged to a safe test voltage which does not exceed safe handling levels.

Figure 10:
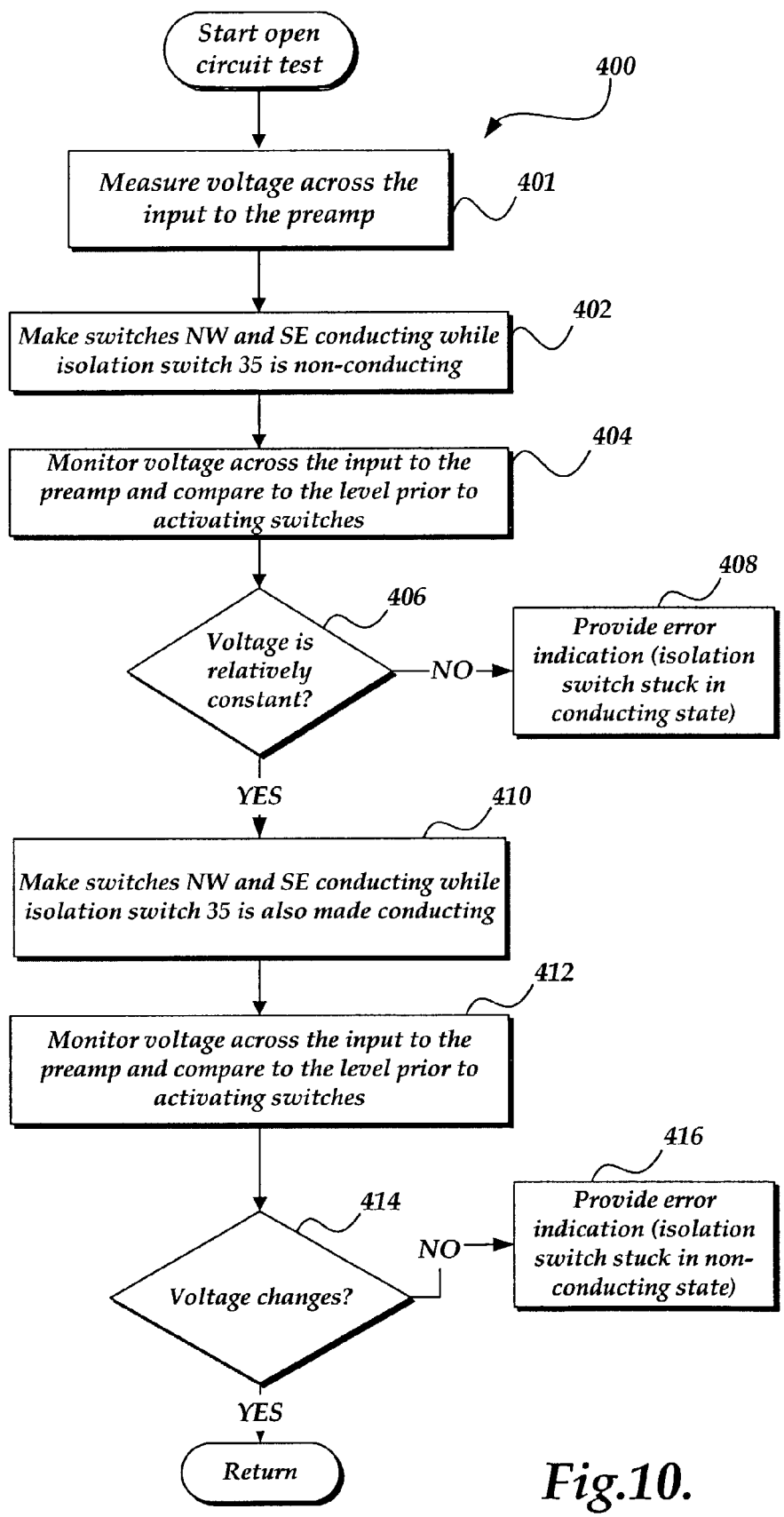
FIG. 10 is a flow diagram illustrating an alternate embodiment of a self-test for an isolation switch when an open-circuit load impedance is detected.

FIG. 10 shows a flow diagram of a self-test 400 for the isolation switch 35 when an open circuit is detected for the load impedance. At a block 401, a voltage across the input to the preamp of the impedance circuit 37 is measured. At a block 402, the switches NW and SE are made conducting while the isolation switch 35 is nonconducting. At a block 404, the voltage across the input to the preamp is monitored and compared to the level prior to activating the switches at block 402. It will be appreciated that the monitoring of the voltage across the input to the preamp at block 404 may be done during the activation of the switches at block 402.

At a decision block 406, the routine determines whether the voltage across the input to the preamp was relatively constant. If the voltage across the input to the preamp was not relatively constant, then the routine proceeds to a block 408, where an error indication is provided, as the indication is that the isolation switch may be stuck in a conducting state. If at decision block 406 it is determined that the voltage across the input to the preamp was relatively constant, then the routine proceeds to a block 410.

At block 410, the routine makes the switches NW and SE conducting while the isolation switch 35 is also made conducting. At a block 412, the voltage across the input to the preamp is monitored and compared to the level prior to activating the switches at block 410. It will be appreciated that the monitoring of the voltage at block 412 may be done during the activation of the switches at block 410.

At a decision block 414, the routine determines whether the voltage across the input to the preamp has changed. If the voltage has not changed, then the routine proceeds to a block 416 where an error indication is provided, as the indication is that the isolation switch is stuck in a nonconducting state. If at decision block 414 it is determined that the voltage has changed, then the indication is that the relay is conducting and operational, and the routine returns.

The self-test illustrated in FIG. 10 is similar to the self-test described above with reference to FIG. 8. With regard to FIG. 8, the isolation switch can generally be tested using the voltage on the energy storage capacitor to provide the test stimulus. Open- and short-circuit tests could be performed where the capacitor voltage was monitored during the short-circuit tests and the preamplifier was monitored during the open-circuit test. As described above, the self-test of FIG. 10 illustrates another way to perform the open-circuit test by using the impedance channel of the preamplifier as the test stimulus.

In the self-test of FIG. 10, the isolation switch 35 is activated along with the output switches. The output switches form a conducting path through the energy storage capacitor 24 and the inductor 27. If the isolation switch 35 is stuck open, however, the impedance drive current will not be conducted through this path so there is no change in the voltage across the input to the preamplifier. If the isolation switch had closed, the impedance drive current through the switches would have reduced the input voltage to the preamplifier thus indicating a reduction in load impedance. It should be noted that in this self-test the energy storage capacitor is not charged.

As also described above with reference to the self-test of FIG. 10, as another part of the self-test, the isolation switch 35 is not activated when the output switches are turned on. The output switches form a conducting path through the energy storage capacitor 24 and inductor 27. If the isolation switch is stuck closed, however, the impedance drive current will be conducted through this path and the voltage across the input to the preamplifier will be reduced. If the isolation switch had remained open, the impedance drive current would not be conducted through the output switches and the voltage across the input to the preamplifier would be unchanged. It should be noted that the energy storage capacitor in this self-test is not charged, thus conserving energy.

Figure 11:
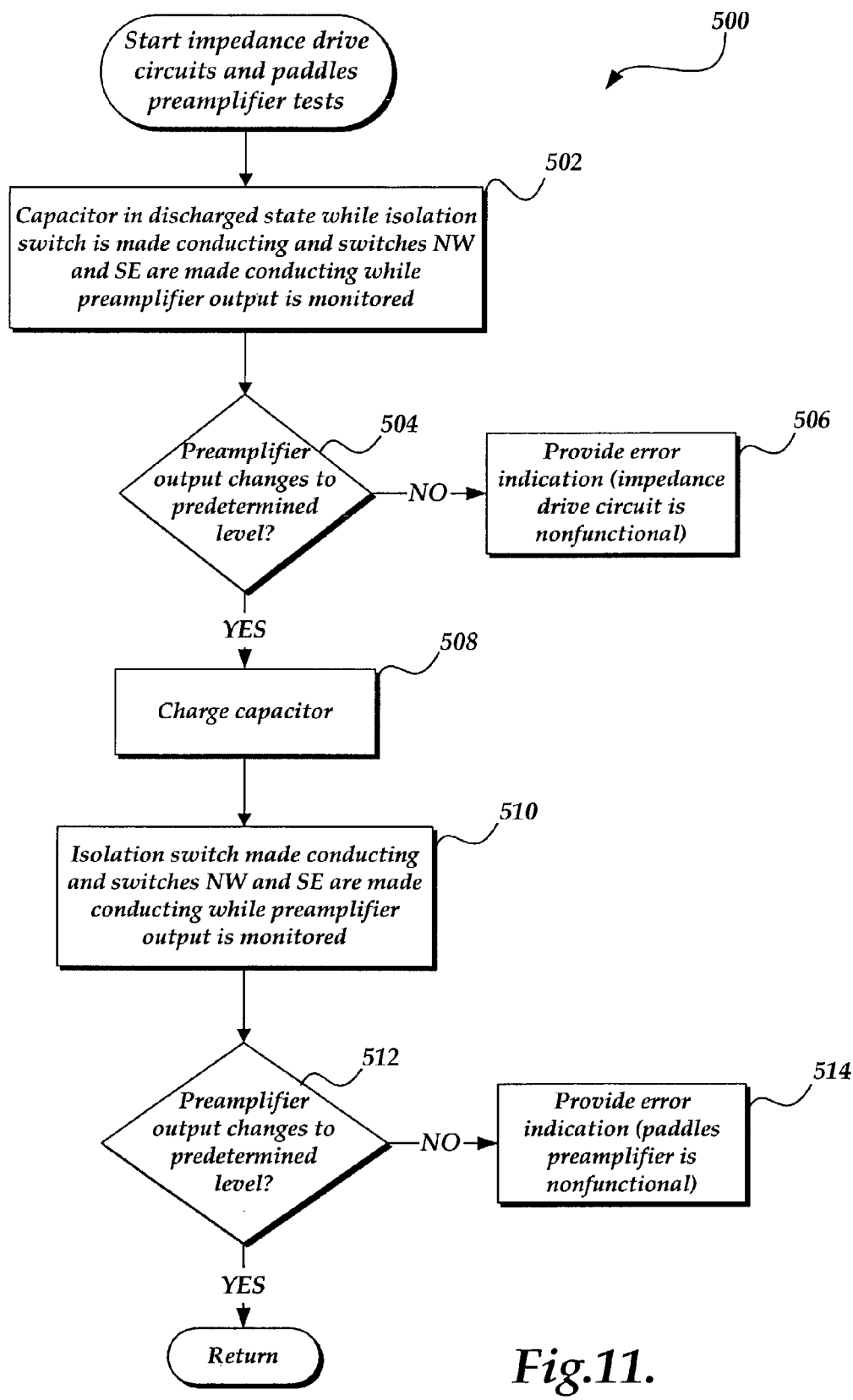
FIG. 11 is a flow diagram illustrating a self-test of an impedance drive circuit and preamplifier.

FIG. 11 shows a self-test 500 of the impedance drive circuits and the paddles preamplifier. In general, the preamplifier is checked when the capacitor voltage is connected across its open circuit input, i.e., the isolation switch is activated and the output switches are turned on. If the preamplifier is functional, the preamplifier output will change to a predetermined level when the voltage is across its input. The impedance drive and measurement circuit is checked by the same process except the energy storage capacitor is not charged. If the impedance drive circuit is functional, then the preamplifier output will change to a predetermined level. It will be appreciated that the unique features of the self-test 500 include that the test does not require any internal or external test circuits as it tests and checks the complete preamplifier and impedance channel. Certain prior art defibrillators that utilize a special built-in test circuit that generates a test stimulus into the second stage of the ECG channel, require a test circuit that is able to withstand the high voltages that can occur during actual use.

In FIG. 11, the impedance drive and measurement circuit is checked first, followed by the check of the preamplifier. It will be appreciated that these circuits may be tested separately or in different orders. In FIG. 11, at a block 502, while the capacitor is in a discharged state the isolation switch is made conducting and the switches NW and SE are made conducting while the preamplifier output is monitored. At a decision block 504, the routine determines whether the preamplifier output changes to a predetermined level. If the preamplifier output changes, then the routine proceeds to a block 506 where an error indication is provided, indicating that the impedance drive circuit is nonfunctional. If the preamplifier output does change, then the routine proceeds to a block 508.

At a block 508, the capacitor is charged. At a block 510, the isolation switch is made conducting and the switches NW and SE are made conducting while the preamplifier output is monitored. At a decision block 512, the routine determines whether the preamplifier output changes to a predetermined level. If the preamplifier output does not change, then the routine proceeds to a block 514, where an error indication is provided, indicating that the paddles preamplifier is nonfunctional. If the preamplifier output does change, then the routine returns.

Figure 12:
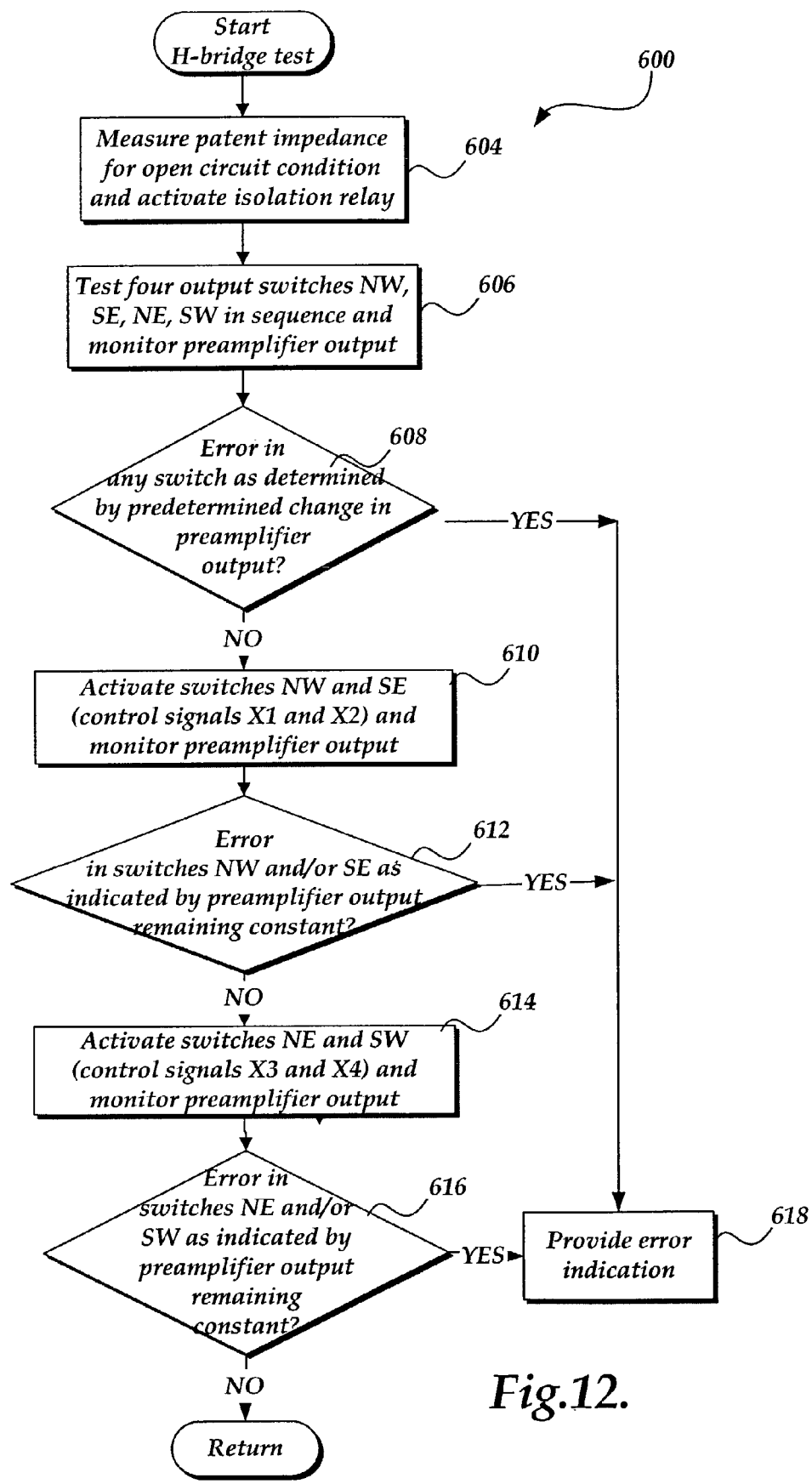
FIG. 12 is a flow diagram of an alternate embodiment of a self-test for an H-bridge.

FIG. 12 illustrates a self-test 600 that is similar to the self-test described above with reference to FIG. 5. In the self-test 600, similar tests of the switch integrity are performed although using the impedance drive circuits and preamplifier, and with an open-circuit load. The energy storage capacitor is not charged. At a block 604, the patient impedance is measured for an open-circuit condition and the isolation relay 35 is activated. At a block 606, each of the four output switches is activated in sequence. The preamplifier output is monitored. A shorted output switch will cause a predetermined change in the preamplifier output. At a decision block 608, the routine determines whether an error has occurred in any of the switches as determined by a predetermined change in the preamplifier output. If an error has occurred, then the routine proceeds to a block 618 where an error indication is provided. If no error has occurred, then the routine continues to a block 610.

At block 610, control signals X1 and X2 are used to activate switches NW and SE. The preamplifier output is monitored. If either or both of the switches are stuck in a nonconducting state, the preamplifier output will remain constant. If both of the switches are functional, then the switches will conduct and cause a predetermined change in the preamplifier output. Thus, at decision block 612, the routine determines whether an error has occurred in switches NW and/or SE as indicated by the preamplifier output remaining constant. If an error has occurred, then the routine proceeds to block 618 where an error indication is provided. If no error has occurred, then the routine proceeds to a block 614.

At block 614, the control signals X3 and X4 are used to activate the switches NE and SW. The preamplifier output is monitored. If either or both of the switches are stuck in a nonconducting state, then the preamplifier output will remain constant. If both of the switches are functional, the switches will conduct and cause a predetermined change in the preamplifier output. Thus, at a decision block 616, the routine determines whether an error has occurred in either of the switches NE and/or SW as indicated by the preamplifier output remaining constant. If an error has occurred, then the routine proceeds to block 618 where an error indication is provided. If an error has not occurred, then the routine returns. It will be appreciated that the self-test 600 is particularly advantageous in that it does not require the capacitor to be charged and discharged as part of the self-test, and thus conserves energy in the defibrillator.

It will be appreciated that a primary advantage of the self-tests described above with reference to FIGS. 1–12 is that they provide a method for verifying the integrity of the isolation switch along with the defibrillation and pacing circuitry. The integrity of the isolation switch can be verified regardless of whether the load impedance at the output terminals is measured as an open circuit or a short circuit.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for verifying the integrity of circuitry, including pacing circuitry, in a defibrillator, the defibrillator having an energy storage capacitor and an output circuit with a plurality of switches for coupling the energy storage capacitor to a load, the method comprising verifying the integrity of the pacing circuitry by the steps of:
   providing one or more control signals for making one or more of the switches of the output circuit conducting while one or more control signals for the pacing circuitry are not set to the conducting state;
   measuring a selected energy parameter; and
   if the selected energy parameter changes by more than a predetermined threshold amount, providing an error indication.

2. The method of claim 1, further comprising:
   providing control signals for making one or more of the switches of the output circuit conducting while the control signal for the pacing circuitry is set to the conducting state;
   measuring a selected energy parameter; and
   if the selected energy parameter does not change by at least a predetermined threshold amount, providing an error indication.

3. The method of claim 1, wherein the selected energy parameter is the voltage on the energy storage capacitor.

4. The method of claim 1, wherein the selected energy parameter is not the voltage on the energy storage capacitor.

5. The method of claim 4, wherein the selected energy parameter indicates changes in a pacing current.

6. The method of claim 1, wherein the defibrillator further includes defibrillation circuitry, and the method further comprises verifying the integrity of the defibrillation circuitry prior to verifying the integrity of the pacing circuitry.

7. The method of claim 1, wherein the defibrillator further includes an isolation switch, and the method further comprises verifying the integrity of the isolation switch after verifying the integrity of the pacing circuitry.

8. The method of claim 7, wherein prior to verifying the integrity of the isolation switch, a measurement of the load across the output of the defibrillator is taken.

9. The method of claim 1, wherein the pacing circuitry comprises a pace current control switch, and one of the control signals for to pacing circuitry controls the pace current control switch.

10. The method of claim 1, wherein the pacing circuitry comprises a pacing relay, and one of the control signals for to pacing circuitry controls the pacing relay.

11. The method of claim 1, wherein the selected energy parameter is the voltage across the input to the preamplifier.

12. A method for testing a pacing switch in a defibrillator, the defibrillator having an energy storage capacitor and an output circuit with a plurality of switches for coupling the energy storage capacitor to a patient, the defibrillator also having an output for applying defibrillation pulses to the patient, the method comprising:
   providing control signals for making one or more of the switches of the output circuit conducting while the control signal for the pacing switch is not set to the conducting state;
   measuring a selected energy parameter that is indicative of the voltage across the output of the defibrillator; and
   if the energy parameter changes by more than a predetermined threshold amount, providing an error indication.

13. A method for testing a pacing switch in a defibrillator, the defibrillator having an energy storage capacitor and an output circuit with a plurality of switches for coupling the energy storage capacitor to a patient, the defibrillator also having an output for applying defibrillation pulses to the patient, the method comprising:
   providing control signals for making one or more of the switches of the output circuit conducting while the control signal for the pacing switch is set to the conducting state;
   measuring an energy parameter that is indicative of the voltage across the output of the defibrillator; and
   if the energy parameter does not change by more than a predetermined threshold amount providing an error indication.

14. A method for verifying the integrity of an isolation switch in a defibrillator, the defibrillator having an energy storage capacitor and an output circuit with a plurality of switches for coupling the energy storage capacitor to the isolation switch, and also having an impedance drive circuit with a preamplifier and an impedance drive current, the method comprising:
   providing control signals for making one or more of the switches of the output circuit conducting while the control signal for the isolation switch is not set to the conducting state;
   measuring a selected energy parameter that is affected by changes in the impedance drive current; and
   if the selected energy parameter changes by more than a predetermined threshold amount, providing an error indication.

15. A method for verifying the integrity of the switches in an H-bridge output circuit of a defibrillator while the output of the defibrillator is in an open circuit state, the method comprising:
   providing a control signal to place an isolation relay in a conducting state;
   providing control signals to make the switches in the H-bridge output circuit conducting such that each leg of the H-bridge output circuit is made to be conducting in sequence;
   monitoring a preamplifier output; and
   if a predetermined change in the preamplifier output is detected, providing an error signal indicating that a switch is stuck in a conducting state.

16. A method for verifying the integrity of the switches in an H-bridge output circuit of a defibrillator while the defibrillator output is in an open circuit state, the method comprising:
   providing control signals to place an isolation relay in a conducting state;
   providing control signals to make the NW and SE legs of the H-bridge output circuit conducting and monitoring a preamplifier output; and
   if the preamplifier output remains relatively constant, providing an error signal indicating that switches in one or both of the NW or SE legs of the H-bridge output circuit are stuck in a nonconducting state.

* * * * *

UNITED STATES PATENT AND TRADEMARK OFFICE
CERTIFICATE OF CORRECTION

PATENT NO. : 7,096,062 B2  Page 1 of 1
APPLICATION NO. : 10/141687
DATED : August 22, 2006
INVENTOR(S) : Patrick F. Kelly et al.

It is certified that error appears in the above-identified patent and that said Letters Patent is hereby corrected as shown below:

On page 2, under "Other Publication", in column 2, line 1, delete "Trucated" and insert -- Truncated --, therefor.

On page 2, under "Other Publication", in column 2, line 4, delete "Stated" and insert -- States --, therefor.

On page 2, under "Other Publication", in column 2, line 8, delete "of" and insert -- for --, therefor.

In column 15, line 49, in Claim 9, delete "to" and insert -- the --, therefor.

In column 15, line 53, in Claim 10, delete "to" and insert --the --, therefor.

In column 16, line 19, in Claim 13, delete "amount" and insert -- amount, --, therefor.

Signed and Sealed this

Twenty-third Day of March, 2010

David J. Kappos
*Director of the United States Patent and Trademark Office*